(12) United States Patent
Pan et al.

(10) Patent No.: US 10,898,420 B2
(45) Date of Patent: Jan. 26, 2021

(54) COMPOSITIONS CONTAINING PHENOLIC COMPOUNDS HAVING SYNERGISTIC ANTIOXIDANT BENEFITS

(71) Applicant: L'OREAL, Paris (FR)

(72) Inventors: Zhi Pan, Clark, NJ (US); Ashleigh Murtaugh, Clark, NJ (US); Fan Hu, Clark, NJ (US); Yan Yu, Clark, NJ (US); Irina Gorodissky, Keyport, NJ (US)

(73) Assignee: L'OREAL, Paris (FR)

( * ) Notice: Subject to any disclaimer, the term of this patent is extended or adjusted under 35 U.S.C. 154(b) by 789 days.

(21) Appl. No.: 15/339,026

(22) Filed: Oct. 31, 2016

(65) Prior Publication Data

US 2018/0116936 A1    May 3, 2018

(51) Int. Cl.

| | |
|---|---|
| *A61K 8/49* | (2006.01) |
| *A61K 8/67* | (2006.01) |
| *A61K 8/365* | (2006.01) |
| *A61Q 19/00* | (2006.01) |
| *A61K 8/06* | (2006.01) |
| *A61K 8/36* | (2006.01) |
| *A61K 8/60* | (2006.01) |
| *A61K 8/97* | (2017.01) |
| *A61Q 19/08* | (2006.01) |

(52) U.S. Cl.
CPC .............. *A61K 8/498* (2013.01); *A61K 8/062* (2013.01); *A61K 8/064* (2013.01); *A61K 8/36* (2013.01); *A61K 8/365* (2013.01); *A61K 8/4926* (2013.01); *A61K 8/4953* (2013.01); *A61K 8/602* (2013.01); *A61K 8/675* (2013.01); *A61K 8/676* (2013.01); *A61K 8/97* (2013.01); *A61Q 19/00* (2013.01); *A61Q 19/08* (2013.01); *A61K 2800/10* (2013.01); *A61K 2800/522* (2013.01); *A61K 2800/592* (2013.01)

(58) Field of Classification Search
CPC .............. A61K 2800/522; A61K 8/365; A61K 8/4953; A61K 8/602; A61K 8/675; A61K 8/676; A61K 2800/10; A61K 2800/592; A61K 8/062; A61K 8/064; A61K 8/36; A61K 8/4926; A61K 8/498; A61K 8/97; A61K 8/06; A61Q 19/00; A61Q 19/08

See application file for complete search history.

(56) References Cited

U.S. PATENT DOCUMENTS

| | | |
|---|---|---|
| 5,824,320 A | 10/1998 | Rouillard et al. |
| 9,072,919 B2 | 7/2015 | Pan et al. |
| 9,107,853 B2 | 8/2015 | Pan et al. |
| 2016/0051459 A1 | 2/2016 | Perassinoto et al. |

FOREIGN PATENT DOCUMENTS

| | | |
|---|---|---|
| CN | 1977855 A | 6/2007 |
| CN | 101019877 A | 8/2007 |
| CN | 103462975 A | 12/2013 |
| CN | 103784356 | 5/2014 |
| EP | 2497481 A1 | 9/2012 |
| ES | 2464192 A1 | 5/2014 |
| WO | 2007124668 A1 | 11/2007 |
| WO | 2014059225 A1 | 4/2014 |
| WO | 2014075866 A2 | 5/2014 |
| WO | 2014165471 A1 | 10/2014 |

OTHER PUBLICATIONS

U.S. Appl. No. 15/827,101, filed Nov. 30, 2017, US20190159989A1, Yang Deng.
Ling, et al. Standardised Mangifera indica extract is an ideal antioxidant Food Chemistry 113 (2009) 1154-1159. journal homepage:www.elsevier.com/locate/foodchem.
International Search Report for PCT/US2017/059273 dated Jan. 8, 2018, 15 pages.
Examination Report communication pursuant to Article 94(3) EPC issued for European Application No. 17804706.4 dated Jun. 3, 2020.

*Primary Examiner* — Aaron J Kosar
(74) *Attorney, Agent, or Firm* — McNees Wallace & Nurick LLC

(57) ABSTRACT

Compositions comprising an isolate or extract comprising mangiferin, one or more of ferulic acid, Vitamin C, and baicalin, present in amounts sufficient to produce synergistic antioxidant activity and provided for cosmetic and other uses.

22 Claims, No Drawings

COMPOSITIONS CONTAINING PHENOLIC COMPOUNDS HAVING SYNERGISTIC ANTIOXIDANT BENEFITS

BACKGROUND OF THE INVENTION

The formation of free radicals is widely considered to play a significant role in the mechanisms of skin aging. Free radicals are highly reactive molecules with unpaired electrons that can directly damage various cellular membranes, lipids, proteins, RNA and DNA. The damaging effects of these reactive oxygen species are induced inside the tissue and cells during normal metabolism and externally through various oxidative stresses. UV exposure and environmental pollution can accelerate skin aging by producing free radicals in skin. Antioxidants protect cells from the damage of oxidative stress by scavenging free radicals and inhibiting oxidation reactions. The topical application of antioxidants is broadly used in skin care products to prevent skin aging. It has been previously shown in the cosmetic related fields that polyphenols act synergistically with other antioxidants such as Vitamin E and carotenoids.

While there are some examples of antioxidants that can provide protective benefits, there remains a need for compositions that offer enhanced options for protective formulations, particularly in the cosmetics arts.

BRIEF SUMMARY OF THE INVENTION

The invention provides compositions comprising (a) Mango Leaf Extract (Mangifera Indica), and at least one of (b) ferulic acid, (c) ascorbic acid (Vitamin C), and (d) baicalin, where (a) and one or more of (b)-(d) are present in the compositions in amounts sufficient to produce synergistic antioxidant activity.

In some embodiments, the invention provides compositions comprising (a) an isolate or extract comprising mangiferin up to 100% in purity, and at least one of (b) ferulic acid, (c) ascorbic acid (Vitamin C), and (d) baicalin, where (a) and one or more of (b)-(d) are present in the compositions in amounts sufficient to produce synergistic antioxidant activity.

The compositions can also contain additional antioxidants. The invention thus also provides compositions comprising (a) an isolate or extract comprising mangiferin up to 100% in purity, and at least one of (b) ferulic acid, (c) Vitamin C, and (d) baicalin, present in the compositions in amounts sufficient to produce synergistic antioxidant effect, and (e) one or more additional antioxidant different than (a)-(d).

In accordance with some embodiments, the compositions include (a) about 0.01% to about 20% of an isolate or extract comprising mangiferin up to 100% in purity, and one or more of (b) about 0.01% to about 20% of ferulic acid and (c) about 0.01% to about 20% of Vitamin C, and, (d) about 0.01% to about 20% baicalin, all amounts present as percentages by weight based on the total weight of the composition.

In accordance with some embodiments, the compositions include (a) up to about 10% of an isolate or extract comprising mangiferin up to 100% in purity, and one or more of (b) up to about 10% of ferulic acid, (c) up to about 20% of Vitamin C, and (d) up to about 10% baicalin, present in the composition in amounts sufficient to produce synergistic antioxidant activity, all amounts present as percentages by weight based on the total weight of the composition.

In accordance with some embodiments, the compositions include (a) about 0.5% of an isolate or extract comprising mangiferin up to 100% in purity, and one or more of (b) about 0.5% of ferulic acid and (c) about 10% of Vitamin C, and (d) about 0.5% baicalin, all amounts present as percentages by weight based on the total weight of the composition.

The compositions can optionally contain at least one hydrotrope (f), such as caffeine or nicotinamide that is acceptable for use in cosmetic compositions, and/or at least one glycol.

Another aspect of the invention provides methods for preparing an composition, the method comprising the step of including in the composition (a) an isolate or extract comprising mangiferin up to 100% in purity, and at least one of (b) ferulic acid and (c) Vitamin C, and, (d) baicalin in amounts sufficient to produce synergistic antioxidant activity.

A further aspect of the invention provides methods for preparing a composition, the method comprising the step of including in said composition a hydrotrope (e).

A further aspect of the invention provides methods for preparing an cosmetic formulation comprising an antioxidant composition, the method comprising the step of including in said formulation one or more components for forming one of an aqueous serum, an oil-in-water emulsion, and a water-in-silicone emulsion.

These and other aspects of the invention are set out in the appended claims, and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The term "comprising" (and its grammatical variations) as used herein is used in the inclusive sense of "having" or "including" and not in the exclusive sense of the terms "consisting only of," "consisting essentially of" and "consisting of."

"W/O emulsion," and "W/Si emulsion" as used herein, includes a water phase dispersed in an oil phase, where the oil phase is a continuous phase and includes at least one Si emulsifier.

"Cosmetically acceptable" means compatible with any keratinous substrate. For example, "cosmetically acceptable carrier" means a carrier that is compatible with any keratinous substrate.

The present invention provides compositions comprising (a) an isolate or extract comprising mangiferin up to 100% in purity, and at least one of (b) ferulic acid and (c) Vitamin C, and, (d) baicalin, wherein the (a) an isolate or extract comprising mangiferin up to 100% in purity, and at least one of (b) ferulic acid, and, (c) Vitamin C, and, (d) baicalin are present in amounts sufficient to produce synergistic antioxidant activity.

The compositions may also contain additional antioxidants, hydrotropes, additives and other components, as described herein below.

Applicants have surprisingly found that an isolate or extract comprising mangiferin up to 100% in purity (for example, Mango Leaf Extract), when associated with one or more of Vitamin C, ferulic acid and baicalin, can generate significant synergy to enhance antioxidant activity against reactive oxygen species, especially hydroxyl radical species, as demonstrated in the hydroxyl oxygen radical absorbance capacity (HORAC) assay. Further, we first report here that an isolate or extract comprising mangiferin up to 100% in purity together with ferulic acid and Vitamin C and baicalin demonstrate a strong antioxidant synergy against peroxyl radicals in the oxygen radical absorbance capacity (ORAC) assay and against hydroxyl radical species in the HORAC assay. These surprising synergistic antioxidant effects, in combination with the other known benefits of the compounds individually, can be employed advantageously in cosmetic compositions, particularly for photo protection and oily skin and acne applications. Components and the compositions are more fully described herein below, as are other optional components useful in cosmetic formulations.

Individual components were evaluated for antioxidant activity individually, and in combination, and the results are as presented in the Examples below. Presuming the antioxidant effects would be additive, predictions were made for the combinations and are shown in comparison to the actual activity measured for the inventive combinations in Table 2. Strong synergistic effects were observed only in combinations that included an isolate or extract comprising mangiferin up to 100% in purity, at least one of ferulic acid and Vitamin C, and baicalin, as shown in Samples 1-4 in the Examples. Since these tests were performed on water-based solutions, identified associations between an isolate or extract comprising mangiferin up to 100% in purity, one or more of ferulic acid and Vitamin C, and optionally, baicalin, are ready to be applied in any cosmetic product to provide a stronger protection from free radicals.

The compositions provide stronger protective effects against free radicals and the damaging effects of reactive oxygen species in that the combinations in the compositions herein show synergistic antioxidant activity wherein the activity of an inventive composition is greater than the sum (addition) of the antioxidant activity of each of the components individually.

Synergism was determined by comparing the antioxidant capacities of combinations of components measured by ORAC and HORAC, with expected or additive values of the individual compounds. The HORAC and ORAC assays, respectively, measure two different antioxidant properties, radical chain breaking and prevention of radical formation. The ORAC and HORAC assays are both fluorometric assays that use hydrogen atom transfer chemistry to detect oxidation of a fluorescent probe. In the ORAC assay, a free radical initiator is used to produce peroxyl radical probes, while in the HORAC assay, a hydroxyl radical initiator and fenton reagent are used to produce hydroxyl radical probes.

As reflected in the Examples below, the expected ORAC/HORAC is the combined (additive) antioxidant capacity of each individual antioxidant compound in the association, measured individually and assuming that each is functioning independently. The expected ORAC or HORAC value of a certain association can be calculated by using the following equation: ORAC or HORAC (total)=sum of ORAC or HORAC (compound n, individually) multiplied by the Percentage (compound n, of use in a cosmetic composition), n=1, 2, 3 . . . . Synergistic antioxidant activity is present when a measured ORAC is significantly larger than the expected value. Significantly larger than the expected value refers to measured ORAC or HORAC values at least 25% greater than expected values. In this invention, the compositions as shown in the examples exhibit synergistic antioxidant activity greater than 100%, which is very significant The ORAC assay is one of most commonly used methods to evaluate the capacity of antioxidants against ROS (reactive oxygen species), specific for peroxyl which is one of the most important free radicals present in the human skin environment. The ORAC assay measures the oxidative degradation of the fluorescent probe (fluorescein) after being mixed with free radical generators such as azo-initiator compounds (2,2'-Azobis(2-amidinopropane)dihydrochloride, AAPH). Azo-initiators are considered to produce the peroxyl radical by heating, which damages the fluorescent molecule, resulting in the loss of fluorescence. Antioxidants are considered to protect the fluorescent molecule from the oxidative degeneration. By quantifying the decay of fluorescence using a fluorometer, the degree of protection is determined comparing with a standard control antioxidant Trolox. The result is expressed in µMol equivalent of Trolox. Equipment that can automatically measure and calculate the capacity is commercially available, such as the VarioSkan flash microplate reader from Thermo Scientific.

Similar to the ORAC assay, the HORAC assay is an in tubo assay designed to quantify the capacity of an antioxidant to avert the hydroxyl radical or anti-Fenton reaction. The hydroxyl radical, generated from hydrogen peroxide and Cobalt(II) fluoride (Fenton reaction), will quench a fluorescent probe by a hydrogen atom transfer reaction. Certain antioxidants can chelate the Co(II), preventing the generation of the hydroxyl radical and initially block or prevent the quenching of the probe. By quantifying the decay of fluorescence using a fluorometer, the degree of protection is determined comparing with a standard control antioxidant Gallic acid. The result is expressed in µMol equivalent of Gallic acid. Equipment that can automatically measure and calculate the capacity is commercially available, such as the VarioSkan flash microplate reader from Thermo Scientific.

References disclosing ORAC assays include: Cao G, Alessio H, Cutler R (1993). "Oxygen-radical absorbance capacity assay for antioxidants". Free Radic Biol Med 14 (3): 303-11; Ou B, Hampsch-Woodill M, Prior R (2001). "Development and validation of an improved oxygen radical absorbance capacity assay using fluorescein as the fluorescent probe". J Agric Food Chem 49 (10): 4619-26; Huang D, Ou B, Prior R (2005). "The chemistry behind antioxidant capacity assays". J. Agric. Food Chem. 53 (6): 1841-56; and Garrett A R, Murray B K, Robison R A, O'Neill K L (2010). "Measuring antioxidant capacity using the ORAC and TOSC assays". Advanced Protocols in Oxidative Stress II: Methods in Molecular Biology (series), Donald J Armstrong (ed) 594: 251-62.

References disclosing HOARC assays include: Ciz, Milan and Cizova, Hana (2010). Different methods for control and comparison of the antioxidant properties of vegertables. Food Control, 21, 518-523. Ou, Boxin and Hampash-Woodill, Maureen (2002). Novel fluorometric assay for hydroxyl radical prevention capacity using fluorescein as the probe. Journal of Agricultural and Food Chemistry, 50(10), 2772-2777.

Phenolic Compounds

Phenolic compounds are a structural class of natural, synthetic, and semisynthetic organic compounds that have one or more phenolic constituents. Phenolic compounds containing multiple phenol groups are known as polyphenols. Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are the most plentiful group of polyphenol compounds, making up about two-thirds of the total phenols in consumed feed. Flavonoids are further categorized, according to chemical structure, into chalcones, flavones, flavanones, flavanols, flavonols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, antitumor and antioxidant activities. Flavonoids protect lipids and vital cell components from damaging oxidative stress by efficiently scavenging free radicals.

Non-flavonoid polyphenols include lignans, aurones, stilbenoids, curcuminoids and other phenylpropanoids. Many of them are also well-known antioxidants like resveratrol, curcumin, and pinoresinol.

Other phenolic compounds, in addition to polyphenols, include alkylphenols, betacyanins, capsacinoids, hydroxybenzoketones, methoxyphenols, naphthoquinones, and phenolic terpenes. Some popular examples are ferulic acid, hydroxytyrosol, cinnamic acid, caffeic acid, and p-coumaric acid.

The at least one phenolic compound is solubilized in the compositions, and the amount of phenolic compound will depend on the specific phenolic compound and the type and amount of hydrotrope present in the compositions.

Mango Leaf Extract contains, among other compounds, Mangiferin, a glucosyl xanthone polyphenolic antioxidant that has been demonstrated to have a variety of beneficial properties for cosmetic and therapeutic applications, including, anti-lipid peroxidation, antimicrobial, immunomodulation, cardiotonic, hypotensive, wound healing, antidegenerative and antidiabetic activities. Mango Leaf Extract may be obtained containing mangiferin in amounts from less than 70% and up to 99% or greater. More generally, other isolates and extracts can be obtained that contain mangiferin up to 100% in purity. Thus, it will be appreciated that the descriptor "an isolate or extract comprising mangiferin up to 100% in purity" means and includes, but is not limited to, Mango Leaf Extract.

Thus, in accordance with the various embodiments, as used herein, Mango Leaf Extract means and includes an extract consisting of 100% mangiferin, as well as extracts comprising from less than 70% mangiferin to up to 99% mangiferin. In some representative examples, Mango Leaf Extract may include mangiferin present at 70%, the remainder of the extract comprising other components. Thus, in the various embodiments as disclosed herein, the amount of mangiferin present in inventive compositions can be determined as the product of the weight percent of the Mango Leaf Extract or other isolate or extract reagent used in the formulation and the percentage of mangiferin in the selected reagent. Thus, for example, inventive compositions comprising 0.5% Mango Leaf Extract prepared with a reagent that comprises 70% mangiferin, would comprise about 0.35% mangiferin together with other components of the Mango Leaf Extract. In some embodiments, mangiferin is provided having purity from less than 70% and up to greater than 99%, alone or together with other components, for example, in isolates or extracts from sources other than Mango Leaf. It will be appreciated that compositions according to the invention may comprise mango leaf extract or other isolates or extracts containing mangiferin. Thus, in another example, inventive compositions comprising 1% of an isolate or other extract prepared with a reagent that comprises 100% mangiferin, would comprise about 1% mangiferin essentially free from other components in the isolate or extract.

More generally, as described herein, extracts comprising other antioxidant compounds of interest such as, but not limited to, ferulic acid, baicalin, and other flavonoids, can be obtained containing one or more antioxidant compounds of interest in amounts up to 95% or greater. Thus, in accordance with the various embodiments, an extract comprising antioxidant compounds of interest means and includes an extract consisting of 100% of the compound of interest, as well as extracts comprising from less than 70% and up to 100% of the antioxidant compounds of interest. Thus, in the various embodiments as disclosed herein, the amount of an antioxidant compound of interest present in inventive compositions can be determined as the product of the weight percent of the extract reagent used in the formulation and the percentage of the antioxidant compound of interest in the selected reagent.

ferulic acid, which is a hydroxycinnamic acid that can be broadly found in giant fennel, the seeds of coffee, apple, artichoke, peanut, and oranges, as well as in both seeds and cell walls of commelinid plants (such as rice, wheat, oats, and pineapple). Like many natural phenols, it is a strong antioxidant that is very reactive toward free radicals and reduces oxidative stress. Many studies suggest that ferulic acid may have antitumor activity.

*Scutellaria Baicalensis* root extract includes the compound baicalin, which has also been identified as a component of Chinese medicinal herb Huang-chin, is a flavone, a type of flavonoid. It is a potent antioxidant that demonstrates potent effects against oxidative stress diseases, inflammation, allergy, cancer, bacterial infections, etc.

In accordance with the disclosure, the amount of Mango Leaf Extract present in the compositions can range from about 0.01% to about 20%; about 0.01% to about 10%; about 0.01% to about 1%; about 0.1% to about 5%; about 0.1% to about 1%; or about 0.5% to about 5%, based on the total weight of the composition.

In some embodiments in accordance with the disclosure, the amount of an isolate or extract comprising mangiferin up to 100% in purity present in the compositions can range from about 0.01% to about 20%; about 0.01% to about 10%; about 0.01% to about 1%; about 0.1% to about 5%; about 0.1% to about 1%; or about 0.5% to about 5%, based on the total weight of the composition.

In some embodiments in accordance with the disclosure, the amount of mangiferin present in the compositions can range from about 0.01% to about 20%; about 0.01% to about 10%; about 0.01% to about 1%; about 0.1% to about 5%; about 0.1 to about 1%; or about 0.5% to about 5%, based on the total weight of the composition.

In accordance with the disclosure, the amount of ferulic acid present in the compositions can range from about 0.01% to about 20%; about 0.01% to about 10%; about 0.01% to about 1%; about 0.1% to about 5%; about 0.1% to about 1%; or about 0.5% to about 5%, based on the total weight of the composition.

In accordance with the disclosure, the amount of baicalin present in the compositions can range from about 0.01% to about 20%; about 0.01% to about 10%; about 0.01% to about 1%; about 0.1% to about 5%; about 0.1% to about 1%; or about 0.5% to about 5%, based on the total weight of the composition.

Also in accordance with the disclosure, Vitamin C is present in the compositions from about 0.01% to about 20%; about 0.01% to about 15%; about 0.01% to about 10%; about 1% to about 20%; about 1% to about 15%; or about 5% to about 10%, based on the total weight of the composition.

Thus, in various embodiments, any one of the foregoing components selected from Mango Leaf Extract or other isolates or extracts containing mangiferin, ferulic acid, baicalin and Vitamin C is present in an composition according to the disclosure in a weight percent amount from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, to about 20 percent by weight, including increments and ranges therein and there between.

Further, in various embodiments, any one of the specific antioxidant components, such as mangiferin or baicalin, obtained as an extract, for example, Mango Leaf Extract or *Scutellaria Baicalensis* root extract, may be present in an composition according to the disclosure in a weight percent amount that is determined as the product of the percentage purity of the antioxidant in the extract and the percentage of the extract used in the formulation, for example, from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, to about 20 percent by weight, including increments and ranges therein and there between.

Optional Additional Antioxidants

The compositions can also contain one or more additional antioxidants that is/are different from the flavonoid(s) used in the composition and ferulic acid. Additional antioxidants can be any antioxidant suitable for use in cosmetic formulations. Suitable antioxidants include, but are not limited to, resveratrol, tannic acid, polyphenols, amino acids and derivatives thereof, imidazoles, peptides such as carnosine and derivatives, carotenoids, carotenes (such as α-carotene, β-carotene, and lycopene), α-hydroxy acids (such as citric acid, lactic acid, or malic acid), tocopherols and derivatives (such as Vitamin E), vitamin A, co-enzyme Q10, bioflavonoids, glutathione, plant extracts (such as rosemary extract, olive leaf extracts), and green tea extracts.

The amount of additional antioxidants present in the compositions can range from about 0.01% to about 20%; about 0.1% to about 20%; or about 0.01% to about 10%, based on the total weight of the composition.

Optional Hydrotropes

Hydrotropes or glycols may be used in some embodiments to increase solubility of the components of the compositions if solubility of any of the components in water is low. A hydrotrope solution is prepared by completely dissolving one or more hydrotropic agents into water. The component(s) are then added in and mixed using stirring bar or any other mixer. Solubilization of the components occurs within minutes, and mixing continued until clear stable solution is obtained, usually within one hour of mixing. No heat is necessary by following this procedure to dissolve phenolic compounds. Everything is prepared at room temperature to keep the stability of phenolic compounds. This is extremely useful to protect the activity of certain compounds and also makes the process much easier.

Hydrotropes (or hydrotropic agents) are a diverse class of water-soluble compounds that are characterized by an amphiphilic molecular structure and ability to dramatically increase the solubility of poorly soluble organic molecules in water. The at least one hydrotrope is present in the composition in amounts effective to increase the solubility of the phenolic compound in water. At least one hydrotrope refers to one or a combination of two or more hydrotropes. One or a combination of two or more hydrotropes can be used to improve the solubility of phenolic compounds in water. The amount of hydrotrope will vary depending on the hydrotrope and the type and amount of phenolic compound. Increasing the water solubility of the phenolic compound(s) refers to increasing the solubility of the phenolic compound(s) in water in comparison with solubility of the phenolic compound(s) in water in the absence of the hydrotrope or hydrotropes.

An advantage of using hydrotropes is, once a stable solution is obtained, further dilution doesn't influence the stability of the solution. This is very different from organic solvents that are commonly used to increase the water solubility of phenolic compounds, such as polyphenols. Typically, an aqueous dilution of organic solvents with pre-dissolved phenolic compound(s), such as a polyphenol, results in crystallization or precipitation.

Most hydrotropes have aromatic structure with an ionic moiety, while some of them are linear alkyl chains, as listed in the table below. Although hydrotropes noticeably resemble surfactants and have the ability to reduce surface tension, their small hydrophobic units and relatively shorter alkyl chain distinguish them as a separate class of amphiphiles. Consequently, their hydrophobicity is not sufficient enough to create well organized self-associated structures, such as micelles, even with a high concentration.

Common hydrotropic molecules include: sodium 1,3-benzenedisulfonate, sodium benzoate, sodium 4-pyridinecarboxylate, sodium salicylate, sodium benzene sulfonate, caffeine, sodium p-toluene sulfonate, sodium butyl monoglycolsulfate, 4-aminobenzoic acid HCl, sodium cumene sulfonate, N,N-diethylnicotinam ide, N-picolylnicotinam ide, N-allylnicotinam ide, 2-methacryloyloxyethyl phosphorylcholine, resorcinol, butylurea, pyrogallol, N-picolylacetamide 3.5, procaine HCl, proline HCl, nicotinamide, pyridine, 3-picolylamine, sodium ibuprofen, sodium xylenesulfonate, ethyl carbamate, pyridoxal hydrochloride, sodium benzoate, 2-pyrrolidone, ethylurea, N,N-dimethylacetamide, N-methylacetamide, and isoniazid. Hydrotropes can be found in Lee J. et al., "Hydrotropic Solubilization of Paclitaxel: Analysis of Chemical Structures for Hydrotropic Property", Pharmaceutical Research, Vol. 20, No. 7, 2003;

and Lee S. et al., "Hydrotropic Polymers: Synthesis and Characterization of Polymers Containing Picolylnicotinamide Moieties", Macromolecules, 36, 2248-2255, 2003.

Cosmetically acceptable hydrotropes refers to hydrotropes that can be used in cosmetic compositions. While hydrotropes represent a broad class of molecules used in various fields, cosmetic applications will be limited due to safety and tolerance restrictions. Suitable hydrotropes for use in cosmetics include, but are not limited to, nicotinamide (vitamin B3), caffeine, sodium PCA (sodium salt of pyrrolidone carbonic acid), sodium salicylate, urea, and hydroxyethyl urea. The suitability of a hydrotrope for use in cosmetic compositions can be determined using tests known in the art for determining effects on skin, and toxicity to humans.

The amount of hydrotropes present in the compositions can range from about 0.1% to about 20%; about 0.1% to about 10%; or about 1% to about 50%, based on the total weight of the composition.

Optional Additives

The compositions can also comprise at least one additive conventionally used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, fatty acids, such as 18-methyleicosanoic acid, vitamins, panthenol, silicones, vegetable, mineral or synthetic oils, gelling agents, antioxidants, solvents, fragrances, fillers, screening agents, odor absorbers and coloring materials.

These additives can be present in the composition according to the invention in proportions which are not limited, but which advantageously fall in the range from 0 to 50% by weight, or 1 to 50% by weight, with respect to the total weight of the composition.

Water

The compositions comprise from about 1 to about 99.9% by weight of water, with respect to the total weight of the composition. The amount of water in the composition can range from about 1 to 99.5%; about 1 to 60%; or about 1 to 50%, based on the total weight of the composition.

The pH of the compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Formulations Comprising the Compositions

Generally, any composition of the invention can be ingested, injected or topically applied to the skin (over any cutaneous region of the body) or to the mucous membranes (oral, jugal, gingival, genital, conjunctival, and the like). Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, aftershave gels or lotions, depilatory creams, compositions for countering insect stings or bites, pain-relieving compositions or compositions for treating certain skin diseases, such as eczema, rosacea, psoriasis, lichen and severe pruritus.

EXAMPLES

Example 1

TABLE 1

Oxygen & Hydroxyl Radical Absorbance Capacity of selected antioxidant compounds:

| Antioxidant | ORAC (μmolTolox/g) | HORAC (μmolGAE/g) |
| --- | --- | --- |
| Mango Leaf Extract | 8256 | 3325 |
| Vitamin C | 4456 | No activity |
| ferulic acid | 14272 | 9868 |
| baicalin | 4759 | 2592 |

Example 2

TABLE 2

Compositions of tested solution samples:

| Sample # | Antioxidant Association | AOX assay | Expected Value (μmolTrolox/g for ORAC, μmolGAE/g for HORAC) | Measured Value (μmolTrolox/g for ORAC, μmolGAE/g for HORAC) | Increase % |
| --- | --- | --- | --- | --- | --- |
| 1 (new data) | 0.5% Mango Leaf Extract + 0.5% baicalin | HORAC | 30 | 136 | 353% |
| 2 | 0.5% Mango Leaf Extract + 10% Vit C | HORAC | 17 | 154 | 806% |
| 3 | 0.5% Mango Leaf Extract + 0.5% ferulic acid | HORAC | 66 | 222 | 236% |
| 4 | 0.5% Mango Leaf Extract + 10% Vit C + 0.5% ferulic acid | HORAC | 66 | 261 | 295% |

TABLE 2-continued

Compositions of tested solution samples:

| Sample # | Antioxidant Association | AOX assay | Expected Value (μmolTrolox/g for ORAC, μmolGAE/g for HORAC) | Measured Value (μmolTrolox/g for ORAC, μmolGAE/g for HORAC) | Increase % |
|---|---|---|---|---|---|
| 5 | 0.5% Mango Leaf Extract + 0.5% baicalin + 0.5% ferulic acid | ORAC HORAC | 136 for ORAC; 79 for HORAC | 255 for ORAC; 236 for HORAC | 87.50% for ORAC; 198% for HORAC |

The synergy was evident only in the specific combinations including a Mango Leaf Extract, one or more of ferulic acid, Vitamin C, and, baicalin. A synergistic effect was not observed between any two of ferulic acid, Vitamin C, and, baicalin without the association with Mango Leaf Extract.

Example 3: Inventive Serum Formulation with Inventive Compositions

TABLE 3

Serum

| Phase | INCI US | Inventive Sample 1 (wt %) | Inventive Sample 2 (wt %) | Inventive Sample 3 (wt %) | Inventive Sample 4 (wt %) | Inventive Sample 5 (wt %) |
|---|---|---|---|---|---|---|
| | WATER | 88 | 78.5 | 88 | 78 | 87.5 |
| | NIACINAMIDE | 5 | 5 | 5 | 5 | 5 |
| | CAFFEINE | 5 | 5 | 5 | 5 | 5 |
| | FERULIC ACID | | | 0.5 | 0.5 | 0.5 |
| | BAICALIN (*SCUTELLARIA BAICALENSIS* ROOT EXTRACT) | 0.5 | | | | 0.5 |
| | *MANGIFERA INDICA* (MANGO) LEAF EXTRACT | 0.5 | 0.5 | 0.5 | 0.5 | 0.5 |
| | Preservatives | 1 | 1 | 1 | 1 | 1 |
| | ASCORBIC ACID | | 10 | | 10 | |
| | Total | 100 | 100 | 100 | 100 | 100 |

Serum Preparation: Serum (Simplex Formulas that were Tested in Tubo Directly)

Serum was prepared as follows. The components were mixed at room temperature following the sequence listed as above until a clear solution was obtained. Constant stirring was maintained for another >30 min. Good results were obtained with respect to formulation stability according to the foregoing method.

Example 4: Inventive Emulsion Formulations

The compositions according to the disclosure are suitable for integration broadly into different architectures, including, for example, emulsions such as oil-in-water (O/W), and water-in-Silicone emulsion (gel) emulsions for cosmetic use.

Oil-in-Water Emulsion (Cream) Preparation

TABLE 4

Inventive O/W Cream Formulation

| Phase | Component | Weight % of total |
|---|---|---|
| A1 | Water | 57.5 |
| A1 | Nicotinamide | 5 |
| A1 | Caffeine | 5 |
| A1 | ferulic acid | 0.5 |
| A1 | baicalin | 0.5 |
| A1 | Mango Leaf Extract | 0.5 |
| A2 | Glycerin | 10 |
| A2 | Xanthan gum | 0.2 |
| A2 | Preservatives | 1 |
| B | Dicaprylyl carbonate | 3 |
| B | Dimethicone | 3 |
| B | Dicapryl alcohol and ceteareth-20 | 4 |
| B | Glyceryl stearate and PEG-100 stearate | 4.5 |

TABLE 4-continued

Inventive O/W Cream Formulation

| Phase | Component | Weight % of total |
|---|---|---|
| C | Dimethicone ammonium | 4 |
| C | Polyacryloyldim ethyl taurate | 0.3 |
| D | Nylon-12 | 1 |
| | Total | 100 |

Oil-in-water emulsion (cream) Preparation was prepared as follows. Phase A1 components were mixed at room temperature until a clear solution was obtained. In separate containers, Phase A2 was pre-suspended and then added into Phase A1 with constant stirring and heated to 65° C. At the same time, Phase B components were mixed and completely dissolved at 65° C. Then Phase B was added into Phase A and emulsified for 10-15 minutes. Heating was stopped, and mixing was continued when Phase C was added and mixed for another 10 minutes. Phase D was added after the temperature was below 40° C., and mixed for 10-15 minutes (side sweep) or until powders were fully dispersed, and the desired emulsion was obtained.

Water-in-Silicone Emulsion (Gel) Emulsion Preparation:

TABLE 5

Inventive Water-in-Silicone emulsion (gel) Emulsion Formulation

| Phase | Component | Weight % of total |
|---|---|---|
| A | BIS-PEG/PPG-14/14 DIMETHICONE (and) DIMETHICONE | 4 |
| A | Dimethicone (and) dimethiconol | 1 |
| A | Dimethicone | 10 |
| B1 | Water | 42.95 |
| B1 | Nicotinamide | 5 |
| B1 | Caffeine | 5 |
| B1 | Mango Leaf Extract | 0.5 |
| B1 | baicalin | 0.5 |
| B1 | ferulic acid | 0.5 |
| B2 | Glycerin | 15 |
| B2 | Propylene glycol | 5 |
| B3 | Water | 5 |
| B3 | Preservatives | 0.25 |
| B3 | Sodium citrate | 0.2 |
| B3 | Sodium chloride | 0.8 |
| C | Ethanol | 3 |
| C | Preservatives | 0.6 |
| D | Silica silylate | 0.7 |
| | Total | 100 |

Water-in-silicone gel emulsion Preparation was prepared as follows. Phase A components were mixed together at room temperature. Phase B1 and Phase B2 were premixed in separate containers at room temperature until clear solutions were obtained. Phase B3 was mixed while heating it to 75-80° C. until it was clear. Phase B2 and Phase B3 were added into Phase B1 while mixing. Then Phase B was slowly added into Phase A while mixing (as viscosity increased, the mixing speed was appropriately increased). When the addition was finished, mixing was continued for an additional 10 minutes before adding pre-mixed Phase C. Phase D was slowly added while mixing until it was thoroughly dispersed, and the desired emulsion was obtained.

Compositions and formulations as described in the representative embodiment's herein included commercially available materials, including, for example: one of Mango Leaf Extract with from less than 70% and up to 100% mangiferin for example, Mango Leaf Extract with 70% mangiferin, from LAYN; Ascorbic acid from DSM; ferulic acid from ORYZA; baicalin having >95% purity, was obtained from *SCUTELLARIA BAICALENSIS* ROOT EXTRACT from MMP.

What is claimed is:

1. An antioxidant composition comprising:
    (a) an isolate or extract comprising mangiferin; and
    at least one of
    (b) ferulic acid
    (c) Vitamin C;
    (d) baicalin and ferulic acid; or
    (e) ferulic acid and Vitamin C,
    wherein said isolate or extract comprising mangiferin (a), and the at least one of ferulic acid (b), Vitamin C (c), baicalin and ferulic acid, (d) or ferulic acid (b) and Vitamin C (c) are provided in amounts that when combined, are sufficient to produce synergistic antioxidant activity, and
    wherein said composition comprises one or more cosmetically acceptable components for forming the antioxidant composition as one of an aqueous serum, an oil-in-water emulsion, and a water-in-silicone emulsion for topical application to a keratinous substrate.

2. A composition according to claim 1 comprising:
    (a) about 0.01% to about 20% of an isolate or extract comprising mangiferin;
    (b) about 0.01% to about 20% ferulic acid; and
    (c) about 0.01% to about 20% of Vitamin C
    wherein all amounts are percentages by weight based on the total weight of the composition.

3. A composition according to claim 1, comprising:
    (a) about 0.01% to about 20% of an isolate or extract comprising mangiferin;
    (b) about 0.01% to about 20% ferulic acid; and
    (d) about 0.01% to about 20% of baicalin
    wherein all amounts are percentages by weight based on the total weight of the composition.

4. A composition according to claim 1, comprising:
    (a) about 0.01% to about 20% of an isolate or extract comprising mangiferin; and
    (b) about 0.01% to about 20% ferulic acid
    wherein all amounts are percentages by weight based on the total weight of the composition.

5. A composition according to claim 1, comprising:
    (a) about 0.01% to about 20% of an isolate or extract comprising mangiferin; and
    (c) about 0.01% to about 20% of Vitamin C
    wherein all amounts are percentages by weight based on the total weight of the composition.

6. A composition according to claim 1, comprising:
    (a) about 0.01% to about 20% of an isolate or extract comprising mangiferin;
    (b) about 0.01% to about 20% ferulic acid; and
    (d) about 0.01% to about 20% of baicalin
    wherein all amounts are percentages by weight based on the total weight of the composition.

7. A composition according to claim 1, wherein said composition is appropriate for topical application to the skin and is in the form of a lotion, serum, gel, milk, foam, liquid foundation or cream.

8. A composition according to claim 1 further comprising at least one hydrotrope (e).

9. A composition according to claim 8 wherein hydrotrope (e) is caffeine or nicotinamide.

10. A composition according to claim 8 wherein the hydrotrope (d) is present in an amount from about 0.01% to about 20% by weight based on the total weight of the composition.

11. A composition according to claim 1 wherein the isolate or extract comprising mangiferin (a) is present in an amount from about 0.01% to 10% by weight based on the total weight of the composition.

12. A composition according to claim 1 wherein the isolate or extract comprising mangiferin (a) is present in an amount from about 0.01% to 5% by weight based on the total weight of the composition.

13. A composition according to claim 1 wherein one or more of ferulic acid (b) and baicalin (d), when present, is present in an amount from about 0.01% to 10% by weight based on the total weight of the composition, and wherein Vitamin C (c), when present, is present in an amount from about 0.01% to 20% by weight based on the total weight of the composition.

14. A composition according to claim 1 wherein one or more of ferulic acid (b) and baicalin (d), when present, is present in an amount from about 0.01% to 5% by weight based on the total weight of the composition, and wherein Vitamin C (c), when present, is present in an amount from about 5% to 15% by weight based on the total weight of the composition.

15. A composition according to claim 1, wherein mangiferin (a) is present as an extract of mango leaf.

16. A composition according to claim 15, wherein mangiferin (a) is present at a purity of at least about 70% up to about 90%.

17. A composition according to claim 1, comprising:
an antioxidant composition selected from the group consisting of:
(1)
  (a) about 0.5% of mangiferin;
  (b) about 0.5% ferulic acid; and (c) about 10% Vitamin C;
(2)
  (a) about 0.5% of mangiferin; and
  (b) about 10% Vitamin C;
(3)
  (a) about 0.5% of mangiferin; and
  (b) about 0.5% ferulic acid; and
(4)
  (a) about 0.5% of mangiferin; and
  (b) about 0.5% baicalin; and
  (c) about 0.5% ferulic acid;
wherein all amounts are percentages by weight based on the total weight of the composition, and wherein the antioxidant compositions produce synergistic antioxidant activity.

18. A method for preparing a cosmetic formulation comprising an antioxidant composition, comprising:
including in said formulation an antioxidant composition according to claim 1, and further including one or more cosmetically acceptable components for forming one of an aqueous serum, an oil-in-water emulsion, and a water-in-silicone emulsion.

19. A composition comprising:
(a) about 0.5% of an isolate or extract comprising mangiferin; and at east one of
(b) about 0.5% of ferulic acid;
(c) about 10% of Vitamin C; or
(d) about 0.5% of baicalin
wherein all amounts are percentages by weight based on the total weight of the composition, and
wherein said isolate or extract comprising mangiferin (a), and the at least one of ferulic acid (b), Vitamin C (c), or baicalin (d) are provided in amounts that when combined, are sufficient to produce synergistic antioxidant activity, and
wherein said composition comprises one or more cosmetically acceptable components for forming the antioxidant composition as one of an aqueous serum, an oil-in-water emulsion, and a water-in-silicone emulsion for topical application to a keratinous substrate.

20. A method for preparing an antioxidant composition comprising:
including in said composition an isolate or extract comprising mangiferin and at least one of: ferulic acid; Vitamin C; and baicalin and ferulic acid; or Vitamin C and ferulic acid, wherein said isolate or extract comprising mangiferin, and the at least one of ferulic acid; Vitamin C; baicalin and ferulic acid; or Vitamin C and ferulic acid are provided in amounts that when combined, are sufficient to produce synergistic antioxidant activity, and
wherein said composition comprises one or more cosmetically acceptable components for forming the antioxidant composition as one of an aqueous serum, an oil-in-water emulsion, and a water-in-silicone emulsion for topical application to a keratinous substrate.

21. A method according to claim 20, further comprising:
including in said composition one or more additional antioxidants different than mangiferin, ferulic acid, baicalin, and Vitamin C, and a hydrotrope.

22. A composition comprising:
an antioxidant composition selected from the group consisting of:
(1)
  (a) about 0.1% to about 5.0% of mangiferin;
  (b) about 0.1% to about 5.0% of ferulic acid; and (c) about 1.0% to about 15% of Vitamin C;
(2)
  (a) about 0.1% to about 5.0% of mangiferin; and
  (b) about 1.0% to about 15% of Vitamin C;
(3)
  (a) about 0.1% to about 5.0% of mangiferin; and
  (b) about 0.1% to about 5.0% ferulic acid; and
(4)
  (a) about 0.1% to about 5.0% of mangiferin;
  (b) about 0.1% to about 5.0% of baicalin; and
  (c) about 0.1% to about 5.0% of ferulic acid;
wherein all amounts are percentages by weight based on the total weight of the composition, and wherein the antioxidant compositions are present in amounts sufficient to produce synergistic antioxidant activity.

* * * * *